US009675646B2

(12) United States Patent
Bitar

(10) Patent No.: US 9,675,646 B2
(45) Date of Patent: Jun. 13, 2017

(54) TUBULAR BIOENGINEERED SMOOTH MUSCLE STRUCTURES

(71) Applicant: WAKE FOREST UNIVERSITY HEALTH SCIENCES, Winston-Salem, NC (US)

(72) Inventor: Khalil Bitar, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 14/375,818

(22) PCT Filed: Jan. 31, 2013

(86) PCT No.: PCT/US2013/024024
§ 371 (c)(1),
(2) Date: Jul. 31, 2014

(87) PCT Pub. No.: WO2013/116446
PCT Pub. Date: Aug. 8, 2013

(65) Prior Publication Data
US 2014/0379083 A1 Dec. 25, 2014

Related U.S. Application Data

(60) Provisional application No. 61/592,871, filed on Jan. 31, 2012, provisional application No. 61/592,890, filed on Jan. 31, 2012.

(51) Int. Cl.
*A61K 35/34* (2015.01)
*A61L 27/20* (2006.01)
(Continued)

(52) U.S. Cl.
CPC ............... *A61K 35/34* (2013.01); *A61F 2/04* (2013.01); *A61F 2/08* (2013.01); *A61L 27/20* (2013.01);
(Continued)

(58) Field of Classification Search
CPC ........ A61F 2002/041; A61F 2/00; A61F 2/04; A61F 2/042; A61F 2/06; A61F 2/062;
(Continued)

(56) References Cited

U.S. PATENT DOCUMENTS 7,029,689 B2   4/2006  Berglund et al.
7,368,279 B2   5/2008  Bitar et al.
(Continued)

FOREIGN PATENT DOCUMENTS

WO   2011102991 A1   8/2011

OTHER PUBLICATIONS

L'Heureux et al. A completely biological tissue-engineered human blood vessel. The FASEB Journal. 1998. vol. 12 (1):47-56.*
(Continued)

*Primary Examiner* — Christopher D Prone
*Assistant Examiner* — Rokhaya Diop
(74) *Attorney, Agent, or Firm* — Thomas J. Engellenner; Reza Mollaaghababa; Pepper Hamilton LLP

(57) ABSTRACT

Methods of generating tubular, bioengineered, smooth muscle structures are disclosed as well as bioengineered tissue for tubular organ repair or replacement. The methods can include the steps of obtaining smooth muscle cells; culturing the muscle cells to form a smooth muscle cell construct of directionally oriented smooth muscle cells; disposing the smooth muscle cell construct around a tubular scaffold; and culturing construct and scaffold in a growth media until a smooth muscle cell structure is achieved. The step of obtain smooth muscle cells can further include obtaining autologous smooth muscle cells from a subject. In one preferred embodiment, the muscle cells can first be on a fibrin substrate to form a muscle construct, which is then disposed around a tubular scaffold, for example, a chitosan scaffold. The methods of the present invention can further (Continued)

include connecting two or more tubular structures together to form an elongate composite structure.

12 Claims, 3 Drawing Sheets

(51) Int. Cl.
| | |
|---|---|
| C12N 5/00 | (2006.01) |
| C12N 5/077 | (2010.01) |
| A61L 27/38 | (2006.01) |
| A61L 27/50 | (2006.01) |
| C12N 5/0797 | (2010.01) |
| A61F 2/04 | (2013.01) |
| A61F 2/08 | (2006.01) |

(52) U.S. Cl.
CPC ....... *A61L 27/3826* (2013.01); *A61L 27/3873* (2013.01); *A61L 27/50* (2013.01); *C12N 5/0068* (2013.01); *C12N 5/0623* (2013.01); *C12N 5/0661* (2013.01); *A61F 2002/045* (2013.01); *A61L 2430/30* (2013.01); *C12N 2501/999* (2013.01); *C12N 2533/54* (2013.01); *C12N 2533/72* (2013.01)

(58) Field of Classification Search
CPC ........... A61F 2/08; A61F 2002/043–2002/048; A61K 35/34; A61L 27/3873; A61L 27/50; A61L 27/3826; A61L 27/20; C12N 5/0623; C12N 5/0068; C12N 5/0661; C12N 501/999
See application file for complete search history.

(56) References Cited

U.S. PATENT DOCUMENTS

| | | | |
|---|---|---|---|
| 2003/0072741 A1* | 4/2003 | Berglund et al. | ............ 424/93.7 |
| 2005/0209687 A1 | 9/2005 | Sitzmann et al. | |
| 2010/0131075 A1 | 5/2010 | Ludlow et al. | |

OTHER PUBLICATIONS

Zhang et al. A Sandwich Tubular Scaffold Derived From Chitosan For Vessel Tissue Engineering. Journal of Biomedical Materials Research Part A. 2006. vol. 77A (2): 277-284.*
Somara et al. Bioengineered Internal Anal Sphincter Derived From Isolated Human Internal Anal Sphincter Muscle Cells. Gastroenterology. 2009.*
Raghavan et al. Successful Implantation of Bioengineered Intrinsically Innervated Human Internal Anal Sphincter. Gastroenterology. 2011. 141 (1):310-319.*
Sundararajan et al. Porous Chitosan Scaffolds for Tissue Engineering. Biomaterials. 1999 (20):1133-1142.*
Buijtenhuijs, P. et al. "Tissue engineering of blood vessels: characterization of smooth-muscle cells for culturing on collagen-and-elast in based scaffods", Biotechnol. Appl. Biochem., Apr. 2004, vol. 39, pp. 141-149. See abstract: materials and methods, pp. 144, 146.
PCT International Search Report and Written Opinion, PCT/US2013/024024, mailed May 15, 2013 (12 pages).
PCT International Preliminary Report on Patentability and Written Opinion, PCT/US2013/024024, mailed Aug. 14, 2014 (9 pages).
Supplementary European Search Report for corresponding European Application 13743292.8 dated Aug. 18, 2015.
Madihally, Sundararajian et al. "Porous Chitosan Scaffolds For Tissue Engineering", Biomaterials 20 pp. 1133-1142 (1999).
Raghavan, Shreya et al. "Successful Implantation Of Bioengineered, Intrinsically Innervated, Human Internal Anal Sphincter", Gastroenterology 141, pp. 310-319 (2011).
Mang, Ling et al. "A Sandwich Tubular Scaffold Derived From Chitosan For Blood Vessel Tissue Engineering" Wiley Periodicals, Inc. pp. 278-284 (2006).
L'Heureux, Nicolas et al., "A completely Biological Tissue-Engineered Human Blood Vessel", The FASEB Journal, vol. 12, pp. 47-56 (Jan. 1998).

* cited by examiner

TUBULAR BIOENGINEERED SMOOTH MUSCLE STRUCTURES

REFERENCE TO RELATED APPLICATIONS

This application is based upon and claims the priority of U.S. Provisional Patent Application No. 61/592,890, filed Jan. 31, 2012, entitled "Innervation of Engineered Structures, and U.S. Provisional Patent Application No. 61/592,871 filed Jan. 31, 2012, entitled "Tubular Bioengineered Smooth Muscle Structures," which are both hereby incorporated by reference in their entirety.

GOVERNMENT RIGHTS

This invention was made with government support under grant NIH/NIDDK RO1DK042876 awarded by The National Institute of Health. The United States Government has certain rights in the invention.

FIELD OF THE INVENTION

The present invention concerns tissue engineering of tubular structures, such as gastrointestinal (GI) tissues.

BACKGROUND OF THE INVENTION

The human body has numerous tubular structures that perform necessary and vital physiological functions. Smooth muscle cells are the main cell type responsible for proper physiological function of such tubular structures. The body's hollow tubular structures transport body fluids including, for example, blood, urine, hormones and nutrients. Typically, the tubular structure's role is to actively transport these fluids in a unidirectional way without retrograde movement.

For example, such tubular structures include blood vessels that move blood throughout the body. Blood vessels come in different sizes to propel blood through the body and actively contribute to the blood circulation initiated by the heart. The blood vessels fall in two categories: arteries, which transport oxygenated blood away from the heart, and veins, which return oxygen-depleted blood back to the heart. The arteries constitute an integral and important part in the circulation of blood. Veins on the other hand are more passive, and are conduits for continuous flow of blood. However, veins have developed special characteristics to minimize backflow, especially in lower extremities in order to fight gravity.

Several attempts have been made to manufacture blood vessels. Most of the attempts use mesenchymal cells either micro spun or printed or simply seeded on a scaffold. They often fail to generate any propulsive force, and function only as conduits -- with some risk of blockage. Such artificial blood vessels may be suitable for vein replacement but have not been shown to be suitable to artery replacement.

Other examples of tubular structures can be found throughout the digestive system. The hollow organs of the digestive system are highly organized and perform coordinated functions to move food and nutrients. To take full advantage of the nutritional values of the different foods ingested, the food has to be at "the right time in the right place" along the digestive tract for proper breakdown, trituration, digestion and absorption. Any slowdown in this propulsive, peristaltic movement, such as localized or segmental paralysis (referred to as "paresis"), can result in localized or segmental inertia that is detrimental for the proper nutrition and can lead to obstruction, infection or morbidity. Neuromuscular diseases of the gastrointestinal track often exhibit this lack of coordinated propulsive movements. Such disorders can manifest themselves in a variety of locations along the digestive track, e.g., at the level of the esophagus, small intestine or large intestine.

The esophageal conduit extends from the pharynx to the gastroesophageal junction. A lack of peristalsis in the esophagus can lead to hypertensive lower esophageal sphincter (LES). Surgical interventions to remedy long-gap esophageal atresia are often marred by dysmotility and impaired quality of life. In the case of bioengineered esophageal replacements, the restoration of physiological functionality must meet the requirements of both gravitational and peristaltic food transport. This becomes challenging due to the phenomenon of at-will "primary peristalsis," a complex interplay between the central and enteric nervous systems.

Early reports in esophageal wall replacement demonstrated no muscular ingrowth with non-absorbable materials like polytetrafluoroethylene or Dacron. Surface functionalization of these bio-inert prosthetic materials with antigenic collagen typically result in a moderate cellular repopulation at best. Moreover, major side effects associated with the use of these materials have been reported, including stricture formation and inflammatory reactions.

Absorbable biomaterials have also been proposed as esophageal prosthetics to improve biocompatibility and minimize the host-inflammatory response exhibited with fluoropolymers. These were typically extra cellular matrix patches or collagen matrices derived from the urinary bladder or intestinal submucosa. The use of acellular xenogenic extra cellular matrix scaffolds to repair patch defects in the esophageal wall of canine models demonstrated neovascularization and neo-innervation, but no repopulation of esophageal smooth muscle.

Acellular approaches were improved by seeding biomaterials with cells. A modular approach to the regeneration of the esophagus by Saxena et al. used basement membrane matrix coated scaffolds to promote survival and unidirectional alignment of both epithelial cells as well as smooth muscle. Autologous neo-esophagus constructs have been engineered using composite cells (human esophageal epithelial cells, aortic smooth muscle cells and dermal fibroblasts) embedded into porcine tendon collagen or PGA meshes. More recently, Nakase et al. replaced a small portion of resected esophagus using keratinocytes, fibroblasts and smooth muscle cells seeded on human amniotic membrane and PGA sheets.

Although these attempts at tissue engineering displayed better repopulation of constituent cell types and similarities to native esophagus morphology, most segments remain aperistaltic and may cause dysmotility related problems during long-term implantation. In order to externally induce peristalsis, an artificial esophagus have been engineered using nickel-titanium shape memory alloys, and programmed to display peristaltic patterns when implanted in a goat model. Independent experiments using these materials for esophageal reconstruction, however, resulted in stenosis to different degrees. It appears that the paradigm of functional esophageal tissue engineering, if clinically intended to replace long segments, must mandatorily include peristalsis mediated by the intramural and myogenic esophageal components.

Similar problems have plagued attempts to reconstruct intestinal structures. The small intestine is the primary nutrient absorptive structure of the GI tract. Peristalsis and segmental contractions of the small intestine increase the surface area to facilitate greater absorption by the villi of the intestinal epithelium. Loss of intestinal segments due to congenital defects or multiple surgical resections due to inflammation or cancer result in short bowel syndrome. Short segments of small bowel result in malabsorption, malnutrition and adaptive alteration of motility patterns.

Tissue engineering also offers a possible advance to the bowel lengthening surgeries commonly carried out in short bowel syndrome. Collagen sponge scaffolds seeded with autologous smooth muscle cells have been successfully implanted as patch grafts in canine models. These patch grafts regenerated the mucosal and intestinal epithelial layers along with the villi structures. The major problem encountered with these grafts, however, was shrinkage. Dunn et al. used pseudo-tubular structures formed from collagen sponge scaffolds seeded with intestinal smooth muscle cells. The tubular structures were neovascularized within a month after prevascularization in the omentum. Unfortunately, these techniques did not regenerate the enteric neuronal layers, and the smooth muscle cells demonstrated a phenotypic switch to their non-contractile forms.

In one attempt to mimic the epithelium-mesenchyme interactions of GI tract structures, intestinal organoid units have been cultured and seeded onto tubular polymer scaffolds. Vacanti and colleagues implanted tissue-engineered intestine comprised of neonatal rat intestinal organoid units into the omentum of adult rats, and then subsequently implanted these constructs to rescue morbidity resulting from a massive bowel resection. Scaffolds made of small intestinal submucosa and wrapped with omentum were implanted in canine models of short bowel syndrome. These scaffolds repaired patch defects and replaced tubular segments of short bowel, thereby increasing the length of the short bowel. Tissue engineered small intestinal constructs regenerated enteric neuronal plexuses and met basic physiological demands. However, these techniques did not regenerate the alignment of the circular and longitudinal smooth muscle that is crucial to generating appropriate force and motility to facilitate nutrient absorption.

Regeneration of colon segments is similarly elusive. The colon is contiguous with the small intestine, facilitating water absorption and excretion of stool. Loss of colonic segments by surgical resections e.g., to treat aganglionosis (Hirschsprung's Disease) or inflammation significantly alters colonic motility. Disruption of colonic motility alters transit time, resulting in constipation or diarrhea. The idiopathic nature of some of these disease states poses a strong demand for in vitro tissue engineered models of colon, where investigations can be carried out on individual components (smooth muscle, enteric neurons, interstitial cells and mucosa) to understand alterations in pathophysiological conditions. Moreover, alterations in peristalsis and segmental contractions of the colon have direct implications on an individual's quality of life.

Recently, Vacanti et al. reported a tissue engineered colon construct using composite poly lactic and glycolic acid polymers seeded with organoid units isolated from the sigmoid colon. They demonstrated that the tissue engineered conduits have significant absorptive capacity when implanted into animals, but there was no direct measurement of peristalsis or motility.

Although significant advances have been made in tissue engineering of tubular structures, there is a need for better solutions in regeneration of functional smooth muscle structures to maintain various aspects of physiology, like peristalsis, contraction and relaxation. Accordingly, there also exists a need for better techniques for bioengineering of tubular tissues.

SUMMARY OF THE INVENTION

Methods of generating tubular, bioengineered, smooth muscle structures are disclosed as well as bioengineered tissue for tubular organ repair or replacement. The methods can include the steps of obtaining smooth muscle cells; culturing the muscle cells to form a smooth muscle cell construct of directionally oriented smooth muscle cells; disposing the smooth muscle cell construct around a tubular scaffold; and culturing construct and scaffold in a growth media until a smooth muscle cell structure is achieved. The step of obtaining smooth muscle cells can further include obtaining autologous smooth muscle cells from a subject.

In one embodiment, the smooth muscle cells can be deposited around a central post to induce formation of a tubular smooth muscle cell structure. In another embodiment, the muscle cells can first be in a collagen suspension and allowed to gel to form a muscle construct, which is then disposed around a tubular scaffold, for example, a chitosan scaffold.

The methods of the present invention can further include connecting two or more tubular smooth muscle cell structures together to form an elongated composite structure that can be stimulated to produce a travelling wave of contractions through the individual tubular smooth muscle cell structures.

DETAILED DESCRIPTION OF THE INVENTION

Figure 1:
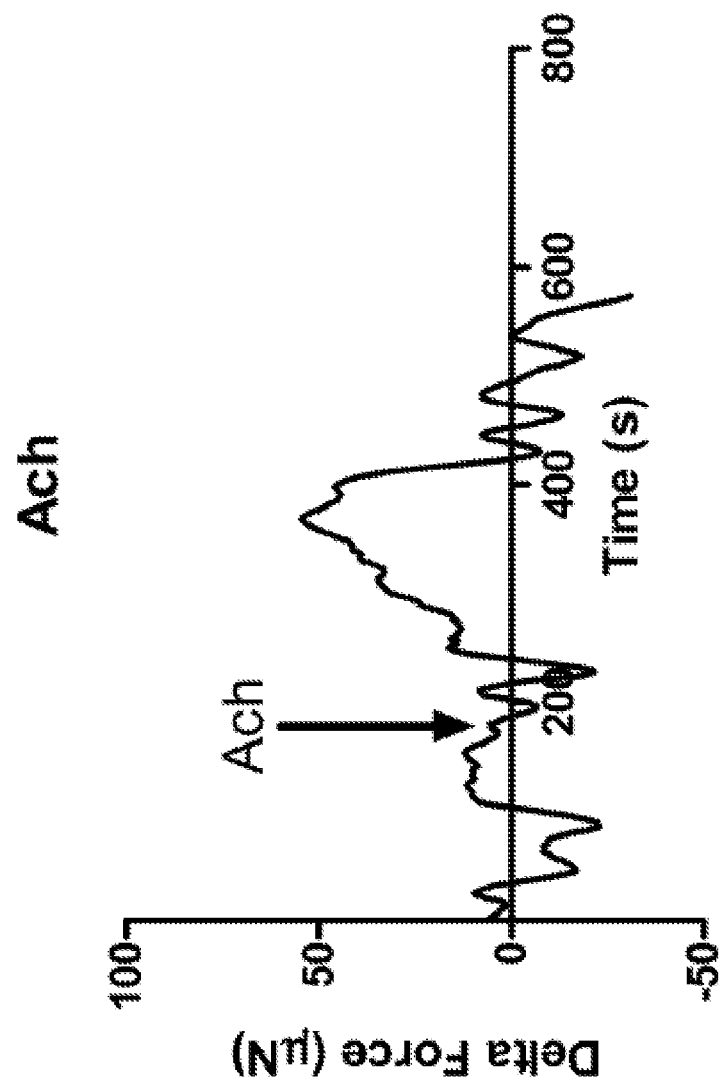
FIG. 1 is a graph showing the cholinergic contraction of a construct according to the invention in response to Acetylcholine (Ach)

Certain exemplary embodiments will now be described to provide an overall understanding of the principles of the structure, function, manufacture, and use of the devices and methods disclosed herein. Those skilled in the art will understand that the devices and methods specifically described herein are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

All publications, patents and patent applications cited herein, whether supra or infra, are hereby incorporated by reference in their entirety. As used in this specification and the appended claims, the singular forms "a," "an," and "the" include plural references unless the content clearly dictates otherwise. The terms used in this invention adhere to standard definitions generally accepted by those having ordinary skill in the art. In case any further explanation might be needed, some terms have been further elucidated below.

The term "subject" as used herein refers to any living organism, including, but not limited to, humans, nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. The term does not denote a particular age or sex. In a specific embodiment, the subject is human.

The terms "treating," "treatment" or "intervention" refer to the administration of one or more therapeutic agents or procedures to a subject who has a condition or disorder or a predisposition toward a condition or disorder, with the purpose to prevent, alleviate, relieve, alter, remedy, ameliorate, improve, affect, slow or stop the progression, slow or stop the worsening of the disease, at least one symptom of condition or disorder, or the predisposition toward the condition or disorder.

Smooth Muscle Cells

One aspect of the invention encompasses generating bioengineered tubular tissues with smooth muscle rings. Physiological models of tubular structures made from smooth muscle tissues that are functionally similar to naturally occurring smooth muscle tissue. Organs or tissues that contain circular smooth muscle may be modeled using the culture system disclosed. Such organs and tissues include the components of the GI tract, e.g., the esophagus, stomach, duodenum, jejunum, ileum and colon. The methods and compositions of the present invention can also be useful in reconstruction of other luminal structures, such as the trachea, bronchial tubes, uterus, blood vessels, lymphatic vessels, urethra, glandular ducts, and the ciliary muscles of the eye.

The term "functionally similar" refers to a bioengineered tubular tissue or tubular tissue encompassing bioengineered smooth muscle rings having similar contractile force or a similar change in contractile isometric force as natural tubular tissue. Contractile force is measured as a peristaltic force or wave-like constrictions/relaxations of the smooth muscle cells of the tubular structure. An agonist may be useful for inducing a contractile response in a smooth muscle cell or induces electrical stimulation in a smooth muscle cell. Contractile response is defined as the decrease in the average length of a smooth muscle cell or smooth muscle tissue. Agonists of contraction include acetycholine, bombesin, substance P, protein kinase C (PKC), endothelins, other neurotransmitters and peptides.

Smooth muscle surrounds the supports of many of the hollow organs. For example, in the gut, smooth muscle surrounds the stomach and intestinal track. Contraction of this muscle mixes food and propels it along the digestive track. In the cardiovascular system, smooth muscle cells surround the walls of the arteries and large veins and functions to control the caliber of the vessels. Smooth muscle lacks the nearly uniform cell shape and lattice-like distribution of skeletal and cardiac muscle cells. However, smooth muscle cells do exhibit an elongated, bipolar cell shape. As a population, smooth muscle cells are organized along a similar axis in a series of overlapping cellular layers. This pattern of organization allows smooth muscle to exert contractile forces in a complex pattern.

The present invention can be employed using isolated primary smooth muscle cells or cell lines derived from such primary cells, tumors and the like. The cells used may be available smooth muscle cell lines such as internal intestinal or anal sphincter smooth muscle cell lines, airway smooth muscle cell lines and other commercially available smooth muscle cell lines. For example, cell lines derived from muscle may be obtained from a cell line depository such as the American Type Culture Collection (ATCC, Bethesda, Md.). Such cell smooth muscle cell lines include human iliac vein smooth muscle cells (HIVS-125; ATCC accession no. CRL-2482), Syrian Golden Hamster ductus deferens smooth muscle cells (DDT1; CRL-1701), human umbical vein smooth muscle cells (HUVS-112D: CRL-2481), rat aorta smooth muscle cells (Hep-Sa; CRL-2018), and human aortic smooth muscle cells (T/G HA-VSMC; CRL-2498). The conditions for growth of the specific cell line purchased will depend on the biological source and generally instructions for the growth of the cells are made available along with the cell lines from ATCC. In other applications, the smooth muscle cells can be obtained from the patient who will be the recipient of the tissue engineering structure. Such autologous cells can be obtained from a surgical excision or a biopsy and can be isolated, cultured, expanded or enriched according to various techniques known in the art.

In one aspect, the isolated cells or cell lines can be pluripotent (obtained by isolation or enrichment or induced dedifferentiation) and able to differentiate into cells that possess contractile function. The cells may be derived from any vertebrate or non-vertebrate animal source. For example, the animal source may be human, monkey or other primate, mouse, rat, rabbit, cat, dog, goat, sheep, pig, horse, cow, fish, bird or any other animal from which such cells may be harvested. In one aspect, the smooth muscle cells used in the three-dimensional culture are mammalian cells. In another aspect, the cells are human or primate cells, but rat and rabbit cells also will be usefully employed herein. The appropriate growth factors may be added to the culture. The concentration of such factors maintained in the cultures can be monitored and adjusted to optimize growth. Cells cultured in this manner can be used for transplantation or implantation in vivo. As noted above, it will often be preferable to obtain the muscle cells from the patient's own tissues (autologous cells).

The invention may be carried out with primary smooth muscle cells isolated from a variety of organs which contain circular smooth muscle. Organs that contain circular smooth muscle include the esophagus, stomach, duodenum, jejumen, ileum, colon, trachea, bronchial tubes, uterus, blood vessels, lymphatic vessels, urethra, glandular ducts, and the ciliary muscle of the eye. For example, smooth muscle cells can be isolated from the internal anal sphincter (IAS) of New Zealand White rabbits as described previously (Bitar et al., Am J Physiol 260: G537-G542, 1991; Bitar et al., Am J Physiol 242: G400-G407, 1982).

The primary cells may be readily isolated by disaggregating an appropriate organ or tissue which is to serve as the source of the cells being grown using standard techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. The digestive enzymes include but are not limited to trypsin, chymotrypsin, collagenase, elastase, and/or hyaluronidase, DNase and pronase. Mechanical disruption can also be accomplished by a number of methods including, but not limited to the use of grinders, blenders, sieves, homogenizers, pressure cells, or sonicators to name but a few. For a review of tissue disaggregation techniques, see Freshney, Culture of Animal Cells. A Manual of Basic Technique, 2d Ed., A. R. Liss, Inc., New York, 1987, Ch. 9, pp. 107-126.

Once the tissue has been reduced to a suspension of individual cells, the suspension can be fractionated into subpopulations from which the myocyte and/or fibroblast cells can be obtained. Fractionation also may be accomplished using standard techniques for cell separation including but not limited to cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, counter current distribution, electrophoresis and fluorescence-activated cell sorting. For a review of clonal selection and cell separation techniques, see Freshney, Culture of Animal Cells. A Manual of Basic Techniques, 2d Ed., A. R. Liss, Inc., New York, 1987, Ch. 11 and 12, pp. 137-168.

To generate the tubular bioengineering structures in culture, the cells can be grown in an appropriate nutrient medium. Many commercially available media such as DMEM, RPMI 1640, Fisher's Iscove's, McCoy's, and the like may be suitable for use. In addition, the three-dimensional structures should be "fed" periodically to remove the spent media and depopulate released cells.

These procedures are greatly facilitated when carried out using a bioreactor, which is a closed system housing the three-dimensional framework inoculated with muscle cells. A bioreactor reduces the possibility of contamination, maintains the cultures under intermittent and periodic pressurization to create environmental conditions that maintain an adequate supply of nutrients to smooth muscle cells throughout the cartilage tissue construct by convection.

Contractile Muscle Tissue Constructs

The tubular tissues disclosed are bioengineered from multiple contractile smooth muscle cell constructs. To generate each contractile smooth muscle cell construct, a homogenous smooth muscle cell population is grown in a cell culture vessel containing one or more extracellular matix proteins. In one embodiment, the smooth muscle cells are grown in fibrin gel, a collagen or a collagen/laminin matrix to produce a transient three-dimensional matrix well suited to the development of each contractile tissue. Fibrin gels are formed by the enzymatic cleavage of fibrinogen by the serine proteinase thrombin allowing the fibrin monomers to interact and form fibrils. Within a fibrin matrix, cells rapidly migrate, proliferate, and digest the fibrin replacing it with their own extracellular matrix (ECM). Grassl et al., Journal of Biomedical Material Research 60: 607-612, 2002. Grassl et al., Journal of Biomedical Materials Research 66A: 550-561, 2003. Neidert et al., Biomaterials 17: 3717-3731, 2002. Ross & Tranquillo Matrix Biology 22: 477-490, 2003).

In one embodiment, the smooth muscle cells can be grown in a collagen or a collagen/laminin matrix. After mixture with the matrix material, the smooth muscle cell population can be cultured to form a layer of smooth muscle cells. The smooth muscle cell population may be cultured to coat a cylindrical ring. In one embodiment, the cylindrical ring can be made of silicone, such as those sold under the trade name Sylgard™. Additionally, the neuronal cell population may be cultured on a silicone treated surface.

The smooth muscle cells can also be grown in a gel to produce a transient three-dimensional matrix. Additionally, the smooth muscle cells can be grown in a fibrin, a collagen or a collagen/laminin matrix to produce a transient three-dimensional matrix. The smooth muscle cell/matrix mixture can be layered over one or more smooth muscle cell layers. Alternatively, the smooth muscle cell/matrix mixture can be cultured as the first layer with a first smooth muscle cell/matrix mixture layered on top of a second smooth muscle cell/matrix mixture.

Matrix proteins, such as fibrin, guide smooth muscle cells to form a ring around a cylindrical mold in culture to form the functional contractile smooth muscle cell construct. The type of matrix that may coat the cylindrical ring and cell culture vessel of the invention is virtually limitless and may include both biological and synthetic matrices. The matrix will have all the features commonly associated with being "biocompatible," in that it is in a form that does not produce an adverse, allergic or other untoward reaction when administered to a mammalian host. Such matrices may be formed from either natural or synthetic materials. In one embodiment, the cylindrical mold can be made of silicone, such as those sold under the trade name Sylgard™.

Tubular Tissue Structures

Individual contractile smooth muscle cell constructs can be assembled to form a tubular tissue structure. The contractile smooth muscle cell constructs can be placed around a tubular scaffold having dimensions appropriate for the tubular tissue contemplated. The number of contractile smooth muscle cell constructs used in the tubular tissue structure varies depending on the size and dimensions of the tubular tissue structure to be bioengineered.

The contractile smooth muscle cell constructs can be joined to form the tubular tissue structure by layering or bonding multiple contractile smooth muscle cell constructs together using standard techniques such as suturing, heating, stapling, and gluing with biological/surgical glue, or a combination of these methods. The contractile smooth muscle cell constructs can also be joined or bonded to a tubular scaffold. Joining, gluing, layering or bonding one or more contractile smooth muscle cell constructs together can also strengthen the tubular tissue structure.

Glues and tissue sealants are well-known in the art and have been commercially available outside the United States for more than a decade. Glues based on gelatins cross linked with formaldehyde have been used experimentally, principally in Europe, since about 1964. Several formulations have been proposed of which "GRF" (gelatin, resorcinol, formol) is best known. Hot solutions of select gelatin are mixed in situ with a curing agent consisting primarily of formaldehyde solution. The mixture rapidly sets to a solid which adheres to tissues.

Fibrin glues utilize the natural processes of blood clot formation to generate an adhesive or sealant composition. One commercial product is "Tussicol"®, Rugis, France. Another is "Fibrin Sealant Kit 1.0" available from Osterreiehisehes Institut fur Ilaemoderivate, GMBH, subsidiary of Immuno AG, A-1220, Vienna, Austria. Two components are combined to form an artificial blood clot. One of the components is a solution of fibrinogen and blood clotting factors such as Factor XIII, and the other is primarily a solution of thrombin and calcium ion.

Tissue Culture Vessels

Those of ordinary skill in the art will readily appreciate that the cell culture and bioengineering methodologies described herein may be carried out in a variety of environments (i.e., vessels or containers). Smooth muscle cells are anchorage dependent, and therefore to grow in culture these cells require a nontoxic, biologically inert, and optically transparent surface that will allow cells to attach and allow movement for growth. Tissue culture vessels or plates include specially-treated polystyrene plastic that are supplied sterile and are disposable. These include Petri dishes, multi-well plates, microtiter plates, roller bottles, screwcap flasks (T-25, T-75, T-150 cm.sup.2 of surface area), culture bags or any container capable of holding cells, preferably in a sterile environment.

In one embodiment of the present invention, a bioreactor is also useful for bioengineering tubular structures and culturing smooth muscle cells. For example, several manufacturers currently make devices that can be used to grow cells and be used in combination with the methods of the present invention. See for example, Celdyne Corp., Houston, Tex.; Unisyn Technologies, Hopkinton, Mass.; Synthecon, Inc. Houston, Tex.; Aastrom Biosciences, Inc. Ann Arbor, Mich.; Wave Biotech LLC, Bedminster, N.J. Further, patents covering such bioreactors include U.S. Pat. Nos. 6,096,532; 6,001,642, 5,985,653; 5,888,807; 5,688,687, 5,605,835, 5,190,878, which are incorporated herein by reference.

There are a number of different kinds of bioreactors, devices designed to provide a low-shear, high nutrient perfusion environment, available on the market. For example, the invention may be carried out in a rotating wall bioreactor, which consists of a small inner cylinder, and the tubular structure, positioned inside a larger outer cylinder. Although the tubular structures of the present invention can be fabricated on the inner cylinder, other locations within the bioreactor also may be used for placement of the construct as well. The gap between the inner and outer cylinders serves as the culture vessel space for cells. Culture medium can be oxygenated via an external hydrophobic membrane. The low shear environment of the rotating bioreactor promotes cell-cell and cell-extracellular matrix (ECM) interactions without the damage or "washing away" of nutrients that occurs with active stirring.

Three-Dimensional Culture System

The three-dimensional culture system of the invention can be used in a variety of applications. In one embodiment, include, the three-dimensional culture system can be used to condition either the individual contractile smooth muscle cell constructs or the bioengineered tubular tissue structures in vitro prior to transplantation or implantation in a subject.

To generate the three-dimensional tubular tissue structures in culture, the cells in the contractile smooth muscle cell constructs or the bioengineered tubular tissue structures must be grown in an appropriate nutrient medium. Many commercially available media such as DMEM, RPMI 1640, Fisher's Iscove's, McCoy's, and the like may be suitable for use. In addition, the three-dimensional cultures should be "fed" periodically to remove the spent media and depopulate released cells.

Those of ordinary skill in the art will readily appreciate that the cell culture and bioengineering methodologies described herein may be carried out in a variety of environments (i.e., vessels or containers). Smooth muscle cells are anchorage dependent, and therefore to grow in culture these cells require a nontoxic, biologically inert, and optically transparent surface that will allow cells to attach and allow movement for growth. Tissue culture vessels or plates include specially-treated polystyrene plastic that are supplied sterile and are disposable. These include Petri dishes, multi-well plates, microtiter plates, roller bottles, screwcap flasks (T-25, T-75, T-150 cm.sup.2 of surface area), culture bags or any container capable of holding cells, preferably in a sterile environment. These procedures are greatly facilitated when carried out using a bioreactor, which can be a closed system housing the three-dimensional framework inoculated with muscle cells. A bioreactor reduces the possibility of contamination, maintains the cultures under intermittent and periodic pressurization to create environmental conditions that maintain an adequate supply of nutrients to smooth muscle cells throughout the cartilage tissue construct by convection.

In one embodiment of the present invention, a bioreactor is also useful for bioengineering segments of the tubular structures by culturing smooth muscle cells. For example, several manufacturers currently make devices that can be used to grow cells and be used in combination with the methods of the present invention.

These methods may be used for generating the contractile smooth muscle cell constructs or the bioengineered tubular tissue structures with smooth muscle cells and may be used to determine if the bioengineered tubular tissue structures are functionally similar to naturally occurring mammalian tubular tissue. In addition, smooth muscle cell function may be measured in vascular muscles as described in Gorenne et al., Amer. J. Physiol. 5:H131-H138, 1998.

Matrix/Scaffold Materials

It is contemplated that each bioengineered contractile smooth muscle cell construct may serve as a component to a larger tubular tissue structure to replace an existing organ. The tubular scaffold used in the formation of the bioengineered tubular tissue structure may be removed prior to transplantation or implantation in a subject or the tubular scaffold may be inserted as part of the bioengineered tubular tissue structure. For insertion of the bioengineered tubular tissue structure into a mammal in need, the matrices used in the formation of the contractile smooth muscle cell construct and/or the scaffold used in the formation of the bioengineered tubular tissue structure may be fabricated from biodegradable materials that will erode over time in the body to yield a completely natural tissue. These matrices and scaffolds will not induce any chronic inflammatory responses, and cannot serve as a long-term site for infection. Biodegradable polymers have been utilized to engineer tissues that will be structurally integrated with the host tissue. A number of naturally-derived matrix-like materials may be used that will eventually biodegrade in an in vivo environment. In addition, the use of synthetic, biodegradable matrices and scaffolds will often be advantageous as the degradation time of such synthetic materials can be designed to coincide with the formation of a new tissue from the cultured cells.

The choice of matrix/scaffold material will differ according to the particular circumstances and the type of smooth muscle cells used or the type of tubular tissue to be bioengineered. Physical and chemical characteristics, such as, e.g., biocompatibility, biodegradability, strength, rigidity, interface properties and even cosmetic appearance, may be considered in choosing a matrix, as is well known to those of skill in the art. Appropriate matrices will act as an in situ scaffolding through which mammalian repair cells may migrate. Matrix/scaffold materials can also be mixtures of more than one material, either mixtures of synthetic materials, synthetic and natural materials, or natural materials.

Fibrin gel is a suitable material that may be used for organ replacement. Fibrin gel is a network made up of monomeric fibrin molecules generated by activation of fibrinogen by thrombin. This biopolymer is known to be involved in hemostatis and wound healing. Fibrin is a biodegradable material that has been used for temporary tissue replacement and as an absorbable implant material.

Another particular example of a suitable material is fibrous collagen, which may be lyophilized following extraction and partial purification from tissue and then sterilized. Matrices may also be prepared from tendon or dermal collagen as may be obtained from a variety of commercial sources, such as, e.g., Sigma and Collagen Corporation.

Collagenous materials useful in the present invention can also be in the form of mineralized collagen. For example, the fibrous collagen implant material termed UltraFiber™ as may be obtained from Norian Corp., (1025 Terra Bella Ave., Mountain View, Calif., 94043) may be used for formation of matrices. U.S. Pat. No. 5,231,169, incorporated herein by reference, describes the preparation of mineralized collagen through the formation of calcium phosphate mineral under mild agitation in situ in the presence of dispersed collagen fibrils.

Another type of biomaterial that may be used is small intestinal submucosa (SIS). The SIS graft material may be prepared from a segment of jejunum of adult pigs. Isolation of tissue samples may be carried out using routine tissue culture techniques such as those described in Badybak et al., (J. Surg. Res. 47:74-80, 1989). SIS material is prepared by removal of mesenteric tissue, inversion of the segment, followed by removal of the mucosa and superficial submucosa by a mechanical abrasion technique. After returning the segment to its original orientation, the serosa and muscle layers are rinsed and stored for further use.

Laminins can also be useful as matrix materials. Laminins are major proteins in the basal lamina, a protein network foundation for most cells and organs. The laminins are an important and biologically active part of the basal lamina, influencing cell differentiation, migration, adhesion as well as phenotype and survival.

Matrices and scaffolds may also be derived from chitin. Chitin, as used herein, refers to a polysaccharide composition prepared from the shells of arthropods, particularly crustacean or insects. It is biocompatible and naturally resorbed by the body, and has been previously used for sustained drug release, bone induction and hemostasis (see e.g. Chandy and Sharma, Biomat. Art. Cells & Immob Biotech. (1991) 19:745-760, Hou et al., Chem. Pharm. Bull. (1985) 33 (9):3986-3992, and Klokkevold, P. J. Oral Maxillofac. Sur. (1992) 50:41-45, the disclosures of which are incorporated herein by reference). Scaffolds may be manufactured with unmodified and/or modified forms chitin.

"Chitosan" is a modified form of chitin and provides one example of a suitable polysaccharide scaffold. "Chitosan," as used herein, includes any polysaccharide produced by hydrolysis of acetamido groups of N-acetyl glucosan in chitin. Also included are scaffolds derived from NOC-chitosan, a water soluble chitin derivative formed by carboxymethylation of biomedical grade chitosan. U.S. Pat. No. 4,619,995, incorporated herein by reference, sets forth the composition and preparation of NOC-chitosan. Chitin and its derivatives can be prepared in powder or solid form from freeze- or air-dried chitin, or from ground chitin as originally produced. Also included are scaffolds derived from cross-linked chitin derivatives (see e.g. Adekogbe, I. "Fabrication and characterization of DTBP-crosslinked chitosan scaffolds for skin tissue engineering" Biomaterials (2005) 26 (35):7241-50, incorporated herein by reference). Other non-limiting examples of chitin scaffolds, and methods for their manufacture, are set forth in U.S. Pat. No. 6,124,273 (disclosing chitin and chitosan hydrogels), U.S. Pat. Nos. 6,699,287 and 6,642,213, the disclosures of which are incorporated by reference.

In various embodiments, the scaffolds can be constructed from a variety of polymer compositions, including, but not limited to, chitosan, chitin, cellulose, alginate, agar, gelatin, soy protein, hyaluronic acid collagen, elastin, and silk alone or in combination with any other polymer composition, in any concentration and in any ratio. In one embodiment, the scaffolds comprise chitosan, either separately or in combination with one or more other materials. In another embodiment, chitosan may be used in combination with other materials, such as with gelatin or alginate.

Possible non-biodegradable matrices/scaffolds include non-biodegradable polymers such as semipermeable polymers such as poly(acrylonitrile-co-vinyl chloride), polylysine, cellulose acetate and polysulfone. Although generally intended for use in immobilized cells, the use of such polymers in the context of the present invention is certainly not excluded. These polymers may also be used with a variety of gels, including alginate and polyphosphazenes. Polyphosphazenes are synthetic polymers, and aqueous solutions of polyphosphazenes will gel in the presence of specific ions. These polymers can be used in the same manner as alginate. The exceedingly stable backbone of these synthetic polymers allows significant alterations in side-group functionality without losing the gentle, physiologic gelling conditions.

There are advantages and disadvantages of both natural materials, e.g., collagens, and synthetic materials, e.g., polyglycolic acids. Synthetic materials that incorporate design concepts or specific biological activities of natural biomaterials may combine the advantages of both types of materials. The reproducible, large-scale synthesis and flexible properties of synthetic polymers can be combined with the biocompatibility and biological activity of natural materials.

The matrix and scaffold materials can be made of the same material or different materials. In one embodiment, the matrix material can be fibrin. In another embodiment, the matrix material can be collagen or collagen/laminin mixture. In yet another embodiment, the scaffold material can be chitosan.

In another embodiment, alginate can be used as a scaffold material, either separately or in combination with one or more other materials. Alginate is easily processed, water soluble, and non-immunogenic. Alginate is a biodegradable anionic polysaccharide with free hydroxyl groups that offer easy gelling. Alginate is a derivative of brown seaweed that has been used for a various medical applications from impression casting in dentistry to medical bandages. The ability to be cast easily and proof of biocompatibility make alginate a desirable material for use in the present invention. Alginate absorbs and holds water well, making it ideal for injury repair where a moist environment is ideal for healing.

Assays for Measuring Smooth Muscle Cell Function

The standard protocols for defining and testing gastrointestinal smooth muscle strips (contraction, relaxation, and spontaneous tone) in vivo are taught in Glavind et al., Am. J. of Physiol. 265: G792-G798, 1993, Glavind et al., Glavind et al., American Journal of Physiology 272: G1075-G1082, 1997, Chakder & Rattan, Am J. Physiol 264: G702-G707, 1993, Knudsen et al., Amer. J. of Physiol. 269: G232-G239, 1995. Following stretch of the muscle strip and a period of equilibrium, spontaneous tension/tone has been described as either steady tension oscillations or stable tension/tone for an extended period of time if undisturbed, accompanied by the ability to contract and relax with the appropriate stimulation. The bioengineered structures of the invention displayed spontaneous tension. Following stretch and stabilization of the baseline tension, bioengineered rings exhibited steady and stable tension/tone over a period of time, and change in the baseline tension was only due to agonist-induced stimuli. The stable tension generated by the rings arbitrarily set to zero for the purposes of consistent force measurements.

These methods may be used for bioengineered tubular tissue structures generated using any circular smooth muscle cells and may be used to determine if the bioengineered structures are functionally similar to naturally occurring mammalian structures or isolated smooth muscle cells, such as exhibiting peristaltic or unidirectional forces. The experimental design of the bioengineered structures is as follows: 1) The bioengineered tubular tissue structure generates a spontaneous basal tone. 2) Upon addition of the relaxant transmitter 8-br-AMP, 8-br-cAMP, the bioengineered structure induces a rapid and significant decrease in the basal tension/basal tone (relaxation) that is measured and expressed as decrease in force generation. 3) Upon addition of acetylcholine, acetylcholine induced a great and immediate generation of force measured (contraction). 4) Addition of 8-br-cAMP-induced rapid relaxation of acetylcholine-induced contraction and force generation of bioengineered structures.

Peristaltic forces or propulsive nature of the bioengineered tubular tissue structures can also be measured by methods known in the art. For example, inserting fluid into the scaffold at one end, while the other end is clamped, will expand the tubular tissue structures at the midsection and allow for unidirectional flow. Upon peristaltic motion of the bioengineered tubular tissue structure, the liquid will be emptied at the opposite end it was inserted, thereby decompressing the midsection. The maximum volume of fluid the bioengineered tubular tissue structures can expel without signs of leakage or backflow can also be measured. Additionally, the fluid pressure can be applied several times to measure for the presence of leakage and backflow.

In some embodiments, the smooth muscle cell function is a patterned motion including at least two evoked contractions at different tubular tissue structures. Optionally, the different tubular smooth muscle structures include adjacent tubular smooth muscle structures and/or remote tubular smooth muscle structures. In some embodiments, the at least two evoked contractions are sequentially and/or timely generated according to a preset sequence. In some embodiments, the smooth muscle cell motion includes a distally advancing contraction wave, optionally though not necessarily including peristalsis. In some embodiments, use of such a system and/or method of smooth muscle cell stimulation diminishes retrograde flow. In some cases, such a method accomplishes this result by stimulating the tubular smooth muscle structures to produce a distally travelling wave of contractions that simulate natural peristalsis.

In addition, smooth muscle cell function may be measured as described in Gorenne et al., Amer. J. Physiol. 5:H131-H138, 1998. For measurement of isometric force, arteries may be cleaned of excess connective tissue, and the endothelium is removed by gently scraping the intima with a cotton swab. Medial strips of swine carotid artery (0.537 mm) are mounted on a Muscle Research Station at room temperature and allowed to equilibrate in PSS for 90 minutes. A passive force of 100 mg is applied to all tissues. After equilibration, tissues are maximally contracted with agonists (50 µM) and then washed in PSS until basal force is recovered. The tissues are then incubated for 2 hours in either PSS or PSS containing an antagonist. After this incubation period, cumulative concentration-response curves to agonists are performed.

EXAMPLES

Example 1

Figure 3:
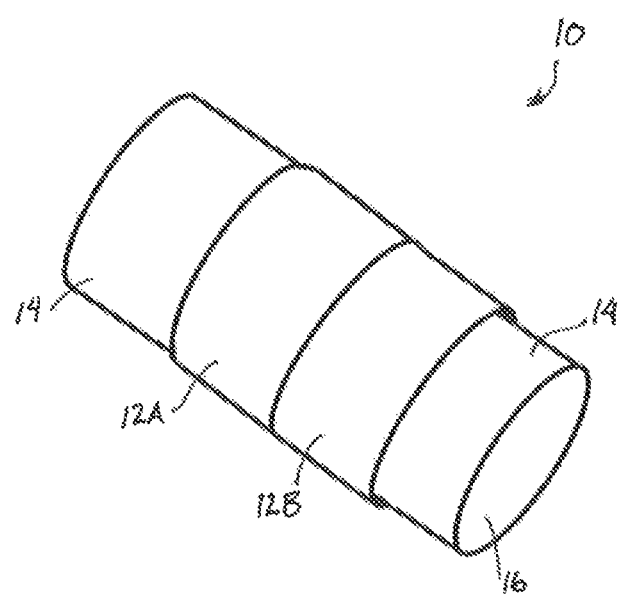
FIG. 3 is a schematic perspective view of a tubular, bioengineered, gastrointestinal tissue structure according to the invention.

As shown schematically in FIG. 3, Several circumferentially-oriented circular smooth muscle cell constructs 12A, 12B were bioengineered using a fibrin-based model with an internal diameter of 5 mm. A hollow tubular chitosan scaffold 14 was also manufactured with the following dimensions: 2.5 cm length, 7.25 mm outer diameter, 3.25 mm luminal diameter and 2 mm thickness. The constructs were placed around the scaffold in close proximity. Surgical glue was applied between the junctions of the constructs and along their circumference. The composite tubular tissue structure 10 was maintained in culture for >2 months. The integrity of the muscle tissue was tested by pipetting media through the lumen 16 and flow and leakage were monitored.

The bioengineered colon segment was 2 cm in length. The construct had a uniform tubular tissue structure similar to native colon. The new bioengineered 2 cm-long circular smooth muscle tubular tissue structure maintained its structural integrity in vitro >2 months. The tubular chitosan scaffold maintained its luminal opening and supported the bioengineered tubular colon around it. Pipetting media through the scaffold from one end, while the other end was clamped, caused an expansion of the cylindrical colon tube at the midsection followed by emptying of the liquid on the opposite end and decompression of the midsection enlargement. The construct was able to withstand a volume 4-5 times the capacity of the relaxed cylinder. There was no sign of leakage from the tissue. The pressure applied several times by pipetting did not cause any leakage and the flow of media was unidirectional without any backflow.

The production of a continuous piece of intestinal smooth muscle, using colonic circular smooth muscle cell constructs that maintained its integrity during the culture period has been shown. There was no leakage through the muscle tissue.

A continuous tubular intestinal smooth muscle tissue structure was manufactured. This structure demonstrated the properties of expansion followed by decompression similar to the mechanical properties of native intestinal tissue. This could be suitable for replacement of any tubular tissue structure that requires the properties of expansion followed by compression. These replacements could be arterial blood vessel, urethra, ureters, and bile ducts. This technology also prides he important of custom made sizes both length and diameters. This is extremely important tin the replacement of small arteries and arterioles where internal diameter is of the essence. Furthermore, these could be made in varying lengths.

Example 2

Tubular esophageal tissue was tissue-engineered to mimic the mechanical and physiological function of a native esophagus. Several concentrically aligned esophageal circular smooth muscle tissue constructs were bioengineered using collagen hydrogel. Three-dimensional smooth muscle tissue constructs were bioengineered. Rabbit esophageal constructs were bioengineered by laying down $5 \times 10^5$ rabbit esophageal circular smooth muscle cells in collagen gel on a Sylgard-coated plate with a central post.

The smooth muscle constructs were placed around a 2.5 cm long hollow chitosan tube and biodegradable surgical glue was applied between the smooth muscle constructs and along their circumference. The constructs were maintained around the scaffold in culture for 5 days.

The constructs were taken off the scaffold and tested to determine cholinergic contraction in response to Acetylcholine (Ach) and relaxation in response to vasoactive intestinal peptide (VIP).

Figure 2:
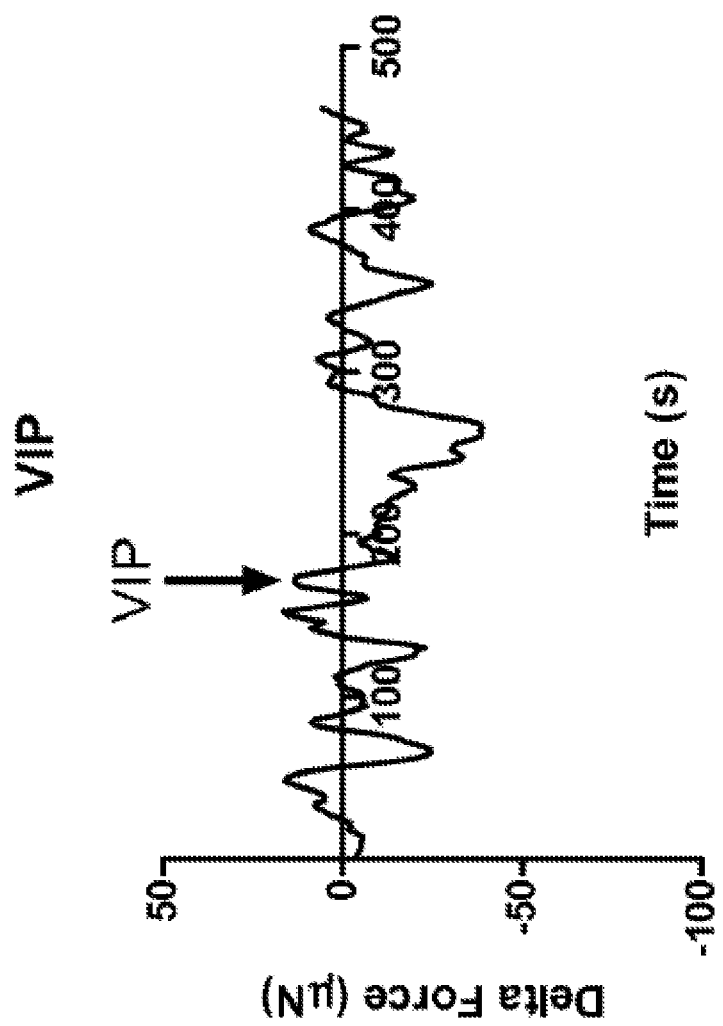
FIG. 2 is a graph showing the relaxation of a construct according to the invention in response to vasoactive intestinal peptide (VIP).

An isometric force transducer (Harvard Apparatus, Holliston, Mass.) was used to record real time force generated by the constructs. The constructs were kept incubated in a warm tissue bath keeping the tissue samples at conditions of 37° C.±1° C. The bioengineered tissue constructs were taken off the scaffold at day 15 for force generation measurement. One side of the tissue constructs was looped around the measuring arm of the transducer and the other side was attached to a fixed reference pin. Tissue constructs were allowed to equilibrate in the tissue bath containing fresh medium. All reported values of force represent active tension produced as a result of the tissue. After establishment of baseline, a 10%-15% stretch was applied to the tissues using the micromanipulator. The stretch baseline established by the tissue samples was arbitrarily set to zero and the values represent change in force generation. Real time force experiments showed that Ach caused a contraction of 45 μN (FIG. 1) and VIP caused a relaxation of −35 μN (FIG. 2).

Semi-solid material was pipetted through the lumen of the tube to check for flow, leakage and muscle integrity. One end of the scaffold was clamped while the other was left intact. The scaffold, with the tissue constructs around it, expanded while pipetting a semi-solid solution through their lumen. The construct was able to restore its original dimensions once the solution was cleared. No signs of leakage were observed and the tissue constructs did not disrupt due to pressure applied from the semi-solid bolus. The bioengineered 2 cm-long esophageal tube construct maintained its luminal patency and its structural integrity in vitro for greater than one month.

What is claimed is:

1. A method of generating a tubular, bioengineered, gastrointestinal tissue structure comprising:
    obtaining smooth muscle cells;
    culturing a first population of the smooth muscle cells to form a first annular smooth muscle cell construct of circumferentially oriented s5mooth muscle cells;
    culturing a second population of the smooth muscle cells to form a second annular smooth muscle cell construct of circumferentially oriented smooth muscle cells;
    joining the first and second annular smooth muscle cell constructs together around a tubular scaffold, wherein the tubular scaffold comprises chitosan; and
    culturing the constructs and scaffold in a growth media until a gastrointestinal tissue structure is achieved that exhibits a travelling wave of contractions through the first and second annular smooth muscle cell constructs in response to a contractile stimulus.

2. The method of claim 1, wherein the step of obtaining smooth muscle cells comprises obtaining smooth muscle cells from a subject.

3. The method of claim 1, wherein the step of culturing the first and second population of smooth muscle cells comprises culturing at least one of said first or second population of the smooth muscle cells in a collagen suspension.

4. The method of claim 1, wherein the first and second annular smooth muscle cell constructs are joined together by a surgical glue.

5. A tubular, gastrointestinal tissue structure formed by the method of claim 1.

6. The method of claim 1 wherein the first and second annular smooth muscle cell constructs are joined together with a gelatin glue.

7. The method of claim 1 wherein the first and second annular smooth muscle cell constructs are joined together with a fibrin glue.

8. The method of claim 1 wherein the first and second annular smooth muscle cell constructs are also bonded to the tubular scaffold.

9. The method of claim 1 wherein the step of culturing the constructs and scaffold in a growth media further comprises culturing the constructs and scaffold in a bioreactor.

10. The method of claim 1 wherein the step of culturing the constructs and scaffold in a growth media further comprises culturing the constructs and scaffold in a low-shear, rotating wall bioreactor.

11. A gastrointestinal tissue structure comprising:
    a first population of smooth muscle cells forming a first annular smooth muscle cell structure;
    a second population of smooth muscle cells forming a second annular smooth muscle cell structure; and
    a tubular scaffold comprising chitosan;
    wherein the first and second annular smooth muscle cell structures are disposed about the scaffold and joined together such that the resulting gastrointestinal smooth muscle tissue structure exhibits circumferentially oriented smooth muscle cells, basal tone and cholinergic contractions in response to a contractile stimulus.

12. The tissue structure of claim 11 wherein the structure also exhibits a travelling wave of contractions through the first and second annular smooth muscle cell constructs in response to a contractile stimulus.

* * * * *